(12) United States Patent
De'Ath et al.

(10) Patent No.: US 6,339,103 B1
(45) Date of Patent: Jan. 15, 2002

(54) FUNGICIDES

(75) Inventors: Norman John De'Ath, Essex (GB); John Klostermyer, Frankfurt am Main (DE); Albert Schirring, PE Haren (NL); Michael Alan Webb; Geoffrey Gower Briggs, both of Essex (GB)

(73) Assignee: Aventis CropScience UK Limited, Cambridge (GB)

( * ) Notice: Subject to any disclaimer, the term of this patent is extended or adjusted under 35 U.S.C. 154(b) by 0 days.

(21) Appl. No.: 09/622,096

(22) PCT Filed: Feb. 18, 1999

(86) PCT No.: PCT/GB99/00338

§ 371 Date: Dec. 12, 2000

§ 102(e) Date: Dec. 12, 2000

(87) PCT Pub. No.: WO99/42468

PCT Pub. Date: Aug. 26, 1999

(30) Foreign Application Priority Data

Feb. 20, 1998 (GB) ............................... 9803491
May 22, 1998 (GB) ............................... 9810932

(51) Int. Cl.⁷ ..................... A61K 31/27; A01N 47/10; C07F 9/02; C07C 271/20

(52) U.S. Cl. ..................... 514/478; 514/479; 560/159; 568/11; 568/13

(58) Field of Search ................. 514/478, 479; 560/159; 568/13, 11

(56) References Cited

U.S. PATENT DOCUMENTS

| | | | |
|---|---|---|---|
| 4,108,885 A | 8/1978 | Hoyer et al. | 260/455 A |
| 4,661,477 A | 4/1987 | Görög né | 514/76 |
| 4,675,431 A | 6/1987 | Görög né | 558/218 |

FOREIGN PATENT DOCUMENTS

| | | |
|---|---|---|
| FR | 2489332 | 3/1982 |
| GB | 1449394 | 9/1976 |
| SA | 98/2863 | 12/1998 |
| WO | 98/44801 | 10/1998 |

OTHER PUBLICATIONS

Couch et al. "Synergistic and antagonistic interactions of fungicides against *Pythium aphanidermatum* on perennial ryegrass," *Crop Protection*, vol. 10, pp. 386–390 (Oct. 1991), published by Butterworth–Heinemann Ltd., Oxford, United Kingdom.

*Primary Examiner*—Sreeni Padmanabhan
*Assistant Examiner*—Brian J. Davis
(74) *Attorney, Agent, or Firm*—Burns, Doane, Swecker & Mathis, L.L.P.

(57) ABSTRACT

The new compound, dimethy[3-(propoxycarbonylamino)propyl]ammonium O-ethylphosphonate, having fungicidal activity, its preparation, compositions comprising it and methods for its use in agriculture.

23 Claims, No Drawings

FUNGICIDES

This invention relates to a new compound having fungicidal activity.

In one aspect, the invention provides the compound, dimethyl-[3-(propoxycarbonylamino)propyl]ammonium O-ethylphosphonate, having the structure

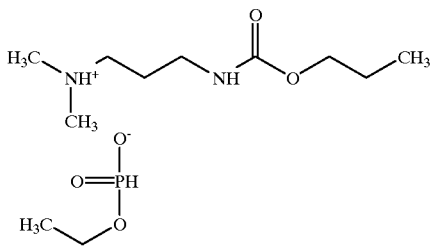

The compound of the invention has activity as a fungicide, especially against Phycomycete diseases of plants, e.g. vine downy mildew (*Plasmopara viticola*), various Phytophthora blights e.g. late tomato or potato blight (*Phytophthora infestans*), Pythium spp., Aphanomyces spp., Bremia spp., Perenospora spp. and Pseudoperenospora spp.

The invention thus also provides a method of combating fungi at a locus infested or liable to be infested therewith, which comprises applying to the locus the compound of formula I.

The invention also provides an agricultural composition comprising the compound of formula I in admixture with an agriculturally acceptable diluent or carrier.

The composition can comprise one or more additional active ingredients, for example compounds known to possess plant-growth regulant, herbicidal, fungicidal, insecticidal or acaricidal properties. Alternatively the compound of the invention can be used in sequence with the other active ingredient.

Fungicides with which the compound can be mixed include acylanilines, such as metalaxyl, oxadixyl, ofurace, benalaxyl and furalaxyl; cymoxanil; mancozeb; chlorothalonil; folpet; captan; famoxadone; fenamidone; spiroxamine; fluazinam; dimethomorph; strobilurins, such as kresoxim-methyl, azoxystrobin and trifloxystrobin, pyrimethanil, cyprodinil; mepanipyrim; and iprodione.

The names quoted for these compounds are the non-proprietary common names and the chemical structure can be found for example by reference to the "Pesticide Manual", eleventh edition, 1997, published by the British Crop Protection Council. Of the compounds whose common names are not mentioned in the Pesticide Manual the full chemical names are as follows:

trifloxystrobin—methyl (E,E)-methoxyimino-{2-[1-(3-trifluoromethylphenyl)-ethylideneaminooxymethyl]phenyl}acetate spiroxamine—8-tert-butyl-1,4-dioxaspiro[4.5]decan-2-ylmethyl(ethyl)-(propyl)amine fenamidone—(S)-1-anilino-4-methyl-2-methylthio-4-phenylimidazolin-5-one The composition of the invention may include for example a dispersing agent, emulsifying agent or wetting agent. Usually they are in the form of an aqueous concentrate.

The concentration of the active ingredient in the composition of the present invention, as applied to plants is preferably within the range of 0.0001 to 1.0 percent by weight, especially 0.0001 to 0.01 percent by weight. In a primary composition, the amount of active ingredient can vary widely and can be, for example, from 5 to 95 percent by weight of the composition.

In the method of the invention the compound is generally applied to seeds, plants or their habitat. Thus, the compound can be applied directly to the soil before, at or after drilling so that the presence of active compound in the soil can control the growth of fungi which may attack seeds. When the soil is treated directly the active compound can be applied in any manner which allows it to be intimately mixed with the soil such as by spraying, by broadcasting a solid form of granules, or by applying the active ingredient at the same time as drilling by inserting it in the same drill as the seeds. A suitable application rate is within the range of from 5 to 1000 g per hectare, more preferably from 10 to 500 g per hectare.

Alternatively the active compound can be applied directly to the plant by, for example, spraying or dusting either at the time when the fungus has begun to appear on the plant or before the appearance of fungus as a protective measure. In both such cases the preferred mode of application is by foliar spraying. It is generally important to obtain good control of fungi in the early stages of plant growth as this is the time when the plant can be most severely damaged. The spray or dust can conveniently contain a pre- or post-emergence herbicide if this is thought necessary. Sometimes, it is practicable to treat the roots of a plant before or during planting, for example, by dipping the roots in a suitable liquid or solid composition. When the active compound is applied directly to the plant a suitable rate of application is from 0.025 to 5 kg per hectare, preferably from 0.05 to 1 kg per hectare.

The compounds of formula I may be obtained by reacting an amine of formula II

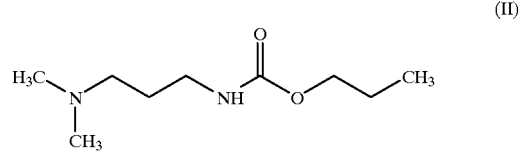

(II)

with ethyl hydrogen phosphonate.

This reaction can be carried out in aqueous solution

The invention is illustrated in the following Example.

EXAMPLE 1

A solution of the sodium salt of ethyl hydrogen phosphonate (13.2 g in water (25 ml)) was added to a an aqueous solution of propyl 3-(dimethylamino)propylcarbamate hydrochloride (31.0 ml of concentration 722 g/l 0.1 moles). The solution was evaporated to dryness to leave an oil containing sodium chloride as a white solid. The crude product was triturated with dichloromethane (ca. 100 ml) and the insoluble white solid (sodium chloride) filtered off and washed with several portions of dichloromethane. The filtrates were combined and evaporated to leave the dimethyl-[3-(propoxycarbonylamino)propyl]ammonium O-ethylphosphonate, as a viscous colourless oil.

Nmr spectroscopy confirmed that the product was a salt by observation of the chemical shifts relative to propyl 3-(dimethylamino)propylcarbamate.

The starting material was prepared by alkaline hydrolysis of diethyl phosphite by a known procedure. See for example Synthesis 134, 1978.

EXAMPLE 2

Aqueous solutions of the compound of Example 1 were sprayed at various concentrations onto vines to run off using a hand-sprayer. Plants were then inoculated by hand spraying with a spore suspension of 100,000 spores per ml of *Plasmopara viticola*. For the purposes of comparison the vines were sprayed also with the commercially available propamocarb hydrochloride.

Plants were assessed for degree of disease control compared with untreated plants.

The results are as follows:

| Treatment | Rate (ppm) | % Control |
| --- | --- | --- |
| Compound of invention | 800 | 81.5 |
| Compound of invention | 400 | 27.6 |
| propamocarb hydrochloride | 800 | 14.6 |
| propamocarb hydrochloride | 400 | 4.2 |

What is claimed is:

1. Dimethyl[3-(propoxycarbonylamino)propyl] ammonium O-ethylphosphonate having the structure

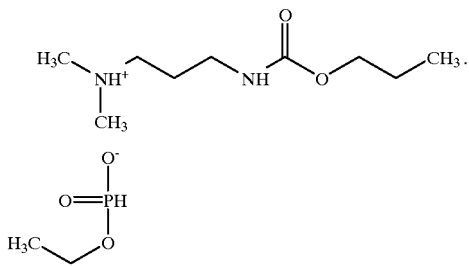

2. A fungicidal composition comprising a fungicidally effective amount of the compound dimethyl[3-(propoxycarbonylamino)propyl]ammonium O-ethylphosphonate having the structure

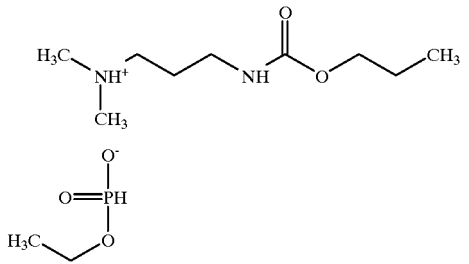

and an agriculturally acceptable diluent or carrier therefor.

3. A composition as claimed in claim 2, further comprising a dispersing agent, an emulsifying agent or a wetting agent.

4. A composition as claimed in claim 3, in the form of an aqueous concentrate.

5. A composition as claimed in claim 2, wherein said compound comprises from 5 percent to 95 percent by weight of the composition.

6. A composition as claimed in claim 2, further comprising one or more additional active ingredients known to have plant-growth regulant, herbicidal, fungicidal, insecticidal or acaricidal properties.

7. A method for the treatment or prevention of fungal disease in plants, seeds or the locus in which they grow or are intended to grow, said method comprising applying to said plants, seeds or locus a fungicidally effective amount of the compound dimethyl[3-(propoxycarbonylamino)propyl] ammonium O-ethylphosphonate having the structure

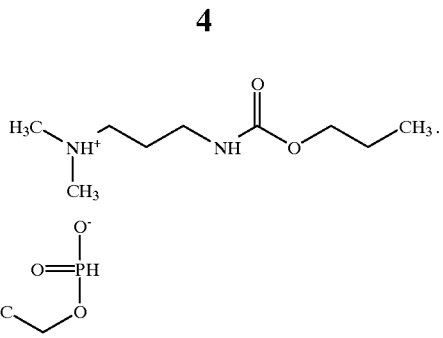

8. A method as claimed in claim 7, wherein said compound is applied in the form of a fungicidal composition comprising said compound and an agriculturally acceptable diluent or carrier therefor.

9. A method as claimed in claim 8, wherein said composition further comprises a dispersing agent, an emulsifying agent or a wetting agent.

10. A method as claimed in claim 9, wherein said composition is in the form of an aqueous concentrate.

11. A method as claimed in claim 8, wherein said compound comprises from 5 percent to 95 percent by weight of said composition.

12. A method as claimed in claim 8, wherein said composition further comprises one or more additional active ingredients known to have plant-growth regulant, herbicidal, fungicidal, insecticidal or acaricidal properties.

13. A method as claimed in claim 8, wherein the concentration of said compound as applied to plants is from 0.0001 percent to 1.0 percent by weight.

14. A method as claimed in claim 13, wherein the concentration of said compound as applied to plants is from 0.0001 percent to 0.01 percent by weight.

15. A method as claimed in claim 7, wherein said compound is applied to the soil before, at or after planting the seed.

16. A method as claimed in claim 15, comprising applying from 5 to 1000 g of said compound per hectare.

17. A method as claimed in claim 16, comprising applying from 10 to 500 g of said compound per hectare.

18. A method as claimed in claim 7, wherein said compound is directly applied to the plant.

19. A method as claimed in claim 18, wherein said compound is applied by foliar spraying.

20. A method as claimed in claim 18, comprising applying from 0.025 to 5 kg per hectare.

21. A method as claimed in claim 20, comprising applying from 0.05 to 1 kg per hectare.

22. A process for preparing the compound as claimed in claim 1, said process comprising reacting an amine having the formula (II)

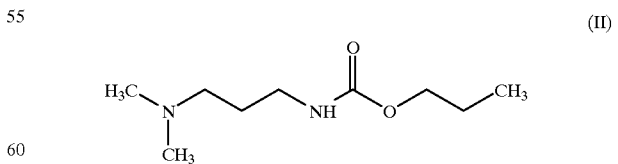

with ethyl hydrogen phosphonate.

23. A process as claimed in claim 22, carried out in aqueous solution.

* * * * *